United States Patent [19]
Tsuchihashi et al.

[11] 3,962,281
[45] June 8, 1976

[54] METHOD OF PREPARING ALDEHYDES

[75] Inventors: Genichi Tsuchihashi, Tama; Katsuyuki Ogura, Sagamihara, both of Japan

[73] Assignee: Sagami Chemical Research Center, Tokyo, Japan

[22] Filed: Aug. 9, 1974

[21] Appl. No.: 496,206

Related U.S. Application Data

[62] Division of Ser. No. 245,305, April 19, 1972, Pat. No. 3,845,076.

[30] Foreign Application Priority Data

Apr. 20, 1971 Japan............................... 46-24910
Apr. 21, 1971 Japan............................... 46-25257
June 2, 1971 Japan............................... 46-37852
Apr. 30, 1971 Japan............................... 46-27998
June 2, 1971 Japan............................... 46-37853

[52] U.S. Cl.......................... 260/340.5; 260/340.3; 260/338; 260/611 A

[51] Int. Cl.².......................................... C07C 43/30
[58] Field of Search............ 260/611 A, 338, 340.3, 260/340.5

[56] References Cited
OTHER PUBLICATIONS

Schultz, et al.: "Chem. Abst.", vol. 73 (1970) col. 98748e.
Ogura, et al., "Chem. Abst.", vol. 75 (1971) col. 118070z.

*Primary Examiner*—Lewis Gotts
*Assistant Examiner*—D. R. Phillips
*Attorney, Agent, or Firm*—Wenderoth, Lind & Ponack

[57] ABSTRACT

A novel method for preparing substituted actaldehydes comprising subjecting a specific sulfoxide derivative to an acidic hydrolysis.

2 Claims, No Drawings

METHOD OF PREPARING ALDEHYDES

This is a division of application Ser. No. 245,305, filed Apr. 19, 1972, now U.S. Pat. No. 3,845,076.

This invention relates to a novel process for producing a substituted acetaldehyde expressed by the general formula

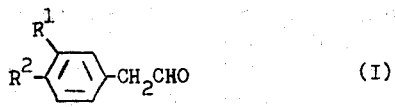

wherein $R^1$ is a hydrogen atom or a lower alkoxy group, $R^2$ is a hydrogen atom, a halogen atom or a lower alkoxy group, and $R^1$ and $R^2$ together may represent a lower alkylidenedioxy group.

Aldehydes of formula (I) are important as intermediates for the synthesis of various organic compounds. For example, p-methoxyphenylacetaldehyde is an important intermediate of Pentazocine, i.e., 2'-hydroxy-5,9-dimethyl-3-(3-methyl-2-butenyl)-6,7-benzomorphan, known as a non-narcotic sedative, and other morphine type sedatives. Phenylacetaldehyde has a perfume like lilac or hyacinth, and can be used as perfume. (3,4-isopropylidenedioxyphenyl) acetaldehyde is novel substance, can, for example, be used advantageously as a starting material for the production of medicine Dopa, i.e., 3-(3',4'-dihydroxyphenyl)-L-alanine and other morphine-type alkaloids.

The method of this invention is based on a novel reaction different from the known methods of producing aldehydes, and can give aldehydes of formula (I) in high purities and yields.

The process of producing aldehydes in accordance with the present invention comprises subjecting to an acidic hydrolysis a sulfoxide having the general formula

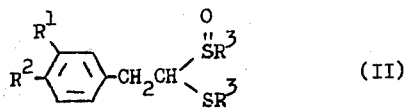

wherein $R^1$ and $R^2$ have the above meanings, and two $R^3$'s are the same and represent a lower alkyl group or a phenyl group to form an aldehyde of formula (I).

In the present specification, the lower alkyl, lower alkoxy and lower alkylidene groups mean groups having 1 to 4 carbon atoms.

The aldehydes of formula (I) produced by the method of this invention include, for example,
p-methoxyphenylacetaldehyde,
p-ethoxyphenylacetaldehyde,
p-bromophenylacetaldehyde,
phenylacetaldehyde,
(3,4-isopropylidenedioxyphenyl)acetaldehyde,
(3,4-methylenedioxyphenyl)acetaldehyde,
(3,4-ethylidenedioxyphenyl)acetaldehyde,
(3,4-dimethoxyphenyl)acetaldehyde,
(3,4-diethoxyphenyl)acetaldehyde,
p-chlorophenylacetaldehyde, and
p-iodophenylacetaldehyde, Especially preferred examples of the starting sulfoxide of formula (II) above include:
methyl 1-methylthio-2-phenylethyl sulfoxide,
methyl 2-(p-halophenyl)-1-methylthioethyl sulfoxide,
methyl 2-(p-methoxyphenyl)-1-methylthioethyl sulfoxide,
methyl 2-(3,4-isopropylidenedioxyphenyl)-1-methylthioethyl sulfoxide,
methyl 2-(3,4-methylenedioxyphenyl)-1-methylthioethyl sulfoxide,
phenyl 2-(3,4-isopropylidenedioxyphenyl)-1-phenylthioethyl sulfoxide
and
isopropyl 2-(3,4-dimethoxyphenyl)-1-isopropylthioethyl sulfoxide.

When the sulfoxide of formula (II) is subjected to an acidic hydrolysis, an aldehyde of formula (I) results. This reaction can be expressed by the following equation

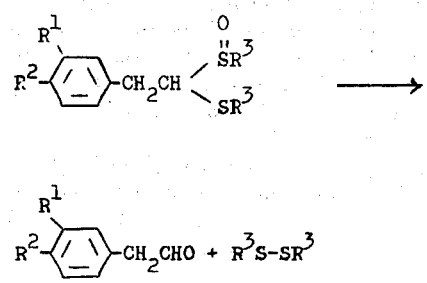

In other words, this reaction is a decomposition catalyzed by an acid, and the presence of water is not altogether necessary. Examples of the preferred acid are mineral acids such as sulfuric acid or hydrochloric acid, and organic acids such as trifluoroacetic acid or para-toluenesulfonic acid. The only requirement here is that the acid should be a protic acid having a pK smaller than about 1, and Lewis acids such as cupric chloride can also be used conveniently. From the economical point of view, hydrochloric acid, sulfuric acid or cupric chloride is preferred. Since the acid acts as a catalyst, its amount may be a catalytic amount. For example, the amount may be as small as about 0.05 equivalent based on the starting sulfoxide. Of course, larger amounts can also be used.

In order to render the operation easy, the above reaction is preferably carried out in a suitable solvent. The suitable solvent is an organic solvent which is chemically inert to the starting materials and reaction products. Examples of such solvent are tetrahydrofuran, alcohols, acetonitrile, ether, dioxane, or 1,2-dimethoxyethane. The reaction temperature is not critical, and usually, temperatures of 0° to 70°C., preferably up to 60°C. are employed. At too low temperatures, the progress of the reaction is slow, and excessively high temperatures only result in an increase in the amounts of by-products. The reaction can proceed smoothly at room temperature, and the aldehyde can be produced within a short period of time. In order to carry out the reaction sufficiently, the reaction time should preferably be from a few hours to 50 hours, although varying depending upon the type of the starting material and the reaction temperature employed.

Isolation of the aldehyde from the resulting reaction mixture can be effected by a conventional recovering means such as the neutralization of the acid catalyst, the removal of the solvent by distillation, the extraction with a suitable extracting solvent, or fractional distillation. One specific embodiment of recovery comprises neutralizing the reaction mixture with a weakly basic substance such as sodium bicarbonate, extracting it with an extracting solvent such as ether or methylene chloride, drying the extracted layer with anhydrous sodium sulfate, evaporating the extracting solvent, and distilling the residue. When a pure substance is required for analytical purposes for example, the resulting product is subjected to column chromatography to give pure aldehyde easily.

The above acid decomposition reaction can be carried out also in the copresence of an acetalization agent, and in this case, the aldehyde of formula (I) can be obtained in the form of the corresponding acetal. For example, when the aldehyde to be obtained is relatively unstable to the acid used as the catalyst, it is preferred that the reaction be performed in the copresence of an acetalization agent such as methyl orthoformate or ethyl orthoformate, and the resulting aldehyde is converted in situ to the corresponding acetal. After completion of the reaction, this acetal derivative, if desired, is treated with a weak acid, and can be converted again to the aldehyde.

The sulfoxide of formula (II) used as the starting material in the process of the present invention can be readily produced by reacting an alpha-halosulfoxide of the formula

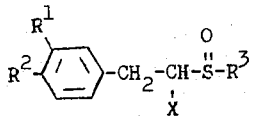

wherein $R^1$, $R^2$ and $R^3$ have the same meanings as described above, and X is a halogen atom, preferably chlorine or bromine; with a thiol or its alkali metal salt of the formula

wherein $R^3$ has the same meaning as described above, and Y is hydrogen or an alkali metal; under the alkaline conditions [see K. Ogura and G. Tsuchihashi, Chem. Commun. 1689 (1970)].

It has now been found that the sulfoxide of formula (II) can also be prepared by the following reaction. This method is novel, and is advantageous in that the material is readily available and the reaction operation is simple as compared with the above-mentioned method. This method comprises reacting a halocompound of the formula

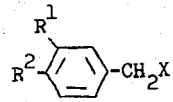

with a compound of the formula

Of the halocompounds of formula (III) used as the starting material in the above reaction, those in which $R^1$ is hydrogen or a lower alkoxy group and $R^2$ is hydrogen, halogen or a lower alkoxy groups include, for example, benzyl halide, p-bromobenzyl halide and p-methoxybenzyl halide. These compounds are commonly used in the chemical industry as reaction agents, and are readily available. On the other hand, those compounds in which $R^1$ and $R^2$ together form a lower alkylidenedioxy group, for example 3,4-methylenedioxybenzyl halide or 3,4-isopropylidenedioxybenzyl halide can be readily synthesized. The 3,4-isopropylidenedioxybenzyl halide is a compound which was synthesized for the first time by the inventors of the present invention. This compound can be prepared by treating 4-methylcatechol with phosphorus pentoxide in acetone, and reacting the resulting 3,4-isopropylidene dioxytoluene with N-bromosuccinimide or t-butyl hypochloride [K. Ogura and G. Tsuchihashi, Tetrahedron Letters, 3151 (1971)].

The compounds of formula (IV), the other material, were also synthesized for the first time by the inventors of the present application. These compounds can be prepared by (a) reacting the compounds of formula $R^3$—SO—$CH_2$X, wherein $R^3$ and X have the meanings mentioned above with the compounds of formula $R^3SY$, wherein $R^3$ and Y have the meanings mentioned above, under the alkaline conditions, or (b) oxidizing the mercaptal of formula $R^3SCH_2SR^3$. The compounds of formula (IV) and the above-described methods (a) and (b) of producing them are described in detail in the copending U.S. patent application Ser. No. 211,100 filed Dec. 22, 1971, now U.S. Pat. No. 3,742,066.

Typical examples of the compounds of formula (IV) include methyl methylthiomethyl sulfoxide, ethyl ethylthiomethyl sulfoxide, isopropyl isopropylthiomethyl sulfoxide and phenyl phenylthiomethyl sulfoxide.

The reaction of forming the sulfoxide of formula (II) from the compounds of formulae (III) and (IV) is carried out in the presence of a metalating agent.

Metalation has been known as the process of attaching a metal atom to a carbon atom of an organic molecule, and the metalating agent is a reagent used in the metalation. The use of a metalating agent in the present invention induces the replacement of the hydrogen atom on the methylene group interposed between the sulfoxide group and the sulfide group in the compound of formula (IV) by an alkali metal. Suitable metalating agents include, for example, alkali metal hydrides such as sodium hydride and alkyl- or aryl-alkali metals such as methyl lithium, butyl lithium and phenyl lithium.

The amount of the metalating agent to be used is about an equivalent to the starting sulfoxide.

The above reaction is preferably carried out in the presence of a solvent. Suitable solvents are aprotic solvents which are chemically inert to the metalating agent, and include, for example, tetrahydrofuran, dimethoxyethane, ethyl ether, dioxane, dimethyl formamide, or benzene. Since the compound of formula (IV) itself has a dissolving action, the reaction can be performed without using a solvent but using an excess of the compound of formula (IV). The reaction temperature that can be employed 15 from −80°C. to +70°C. However, temperature in the range of 0° to 30°C. are especially preferred because no heating or cooling means is necessary, and usually the reaction is carried out at room temperature. The reaction time, although varying according to the reaction conditions, is from about one hour to about 30 hours.

Isolation of the compound of formula (II) from the resulting reaction mixture can be performed by a customary method. For ease of the isolation operation, it is convenient to add methylene chloride, chloroform, or carbon tetrachloride, for example, to the reaction mixture to precipitate by-products such as alkali halides, remove the precipitate by filtration, and remove the solvent from the filtrate by evaporation at reduced pressure.

Where the aldehyde of formula (I) is prepared by acid hydrolysis of the sulfoxide of formula (II), the resulting reaction mixture can be directly used without isolating the compound of formula (II) therefrom.

The following Examples will illustrate the present invention in greater detail.

EXAMPLE 1

2.65 g of methyl 2-(p-methoxyphenyl)-1-methylthioethyl sulfoxide was dissolved in 50 ml. of methanol, and with the addition of 20 ml. of 1N sulfuric acid, the solution was heated for 6 hours at 50°C. The reaction mixture was concentrated at reduced pressure to 20 ml., and extracted with ether (150 ml., 2 times). The extracted layer was washed with water and then with an aqueous solution of sodium hydrogencarbonate, and dried with anhydrous sodium sulfate. It was then concentrated at reduced pressure, and the residue was subjected to column chromatography (silica gel, benzene and methylene chloride) to give 774 mg of p-methoxyphenylacetaldehyde as a colorless liquid. The yield was 53%, b.p. 61°–63°C/2.5 mmHg.

NMR (in $CCl_4$): $\delta$ 3.50 doublet (2H, J=2.7Hz), 3.77 singlet (3H); 6.91$A_2B_2$ quarter (4H, J=8.7 Hz), 9.58 triplet (1H, J=2.7 Hz).

Elemental analysis for $C_9H_{10}O_2$ Calculated: C, 71.98; H, 6.71%. Found: C, 71.13; H, 6.61%.

EXAMPLE 2

764 mg. of methyl 2-(p-methoxyphenyl)-1-methylthioethyl sulfoxide was dissolved in 6 ml. of ethanol, and with the addition of 1.03 ml. of ethyl orthoformate and 5 drops of concentrated sulfuric acid, the solution was stirred for 27 hours at room temperature. 10 ml. of water was added, and the reaction mixture was extracted with methylene chloride. The product was dried with anhydrous sodium sulfate, and concentrated at reduced pressure to give a diethyl acetal of p-methoxyphenylacetaldehyde. 5 ml. of ether was added to the acetal, and 20 ml. of 0.25 N dilute sulfuric acid was further added. The mixture was stirred for 12 hours at room temperature. The stirred mixture was then extracted with ether, and the ether layer was dried with anhydrous sodium sulfate, followed by concentration at reduced pressure. The residue was subjected to column chromatography to give 386 mg of p-methoxyphenylacetaldehyde as a colorless liquid. Yield 82%.

EXAMPLE 3

145 mg of methyl 2-(p-methoxyphenyl)-1-methylthioethyl sulfoxide was dissolved in 5 ml. of ethanol, and with the addition of 2 ml. of 15N dilute sulfuric acid, the solution was allowed to stand for 11 hours at room temperature. The resulting p-methoxyphenylacetaldehyde was converted by a customary method to 2,4-dinitrophenylhydrazone, and analyzed quantitativly. Amount yielded 140 mg; Yield 72%.

EXAMPLE 4

550 mg of methyl 2-(p-bromphenyl)-1-methylthioethyl sulfoxide was dissolved in 5 ml. of ethanol, and with the addition of 0.64 ml. of ethyl orthoformate and 3 drops of concentrated sulfuric acid, the solution was heated for 2 hours at 54°C. 500 mg of sodium hydrogencarbonate was added, and the mixture was stirred for 1 hour at room temperature. The mixture was then filtered, and the filtrate was concentrated at reduced pressure. The residue was subjected to simple distillation to give 437 mg of a diethyl acetal of p-bromophenylacetaldehyde as a colorless liquid.

NMR ($CCl_4$): $\delta$ 1.13 triplet (6H, J=13.5 Hz); 2.77 doublet (2H, J=5.7 Hz); 3.42 quarter (2H, J=13.5 Hz); 4.48 triplet (1H, J=5.7 Hz); 7.18 AB quartet (4H, J=8.7 Hz).

This acetal was subjected to the same procedure as described in Example 2 to give p-bromophenylacetaldehyde. This acetaldehyde was converted by a customary method to 2,4-dinitrophenylhydrazone having a melting point of 155°–156°C. (recrystallized for ethanol).

Elemental analysis for $C_{14}H_{11}BrO_4N_4$: Calculated: C, 44.15; H, 2.86; N, 14.77%. Found: C, 44.34; H, 2.92; N, 14.78%.

EXAMPLE 5

123 mg of methyl 2-(p-bromophenyl)-1-methylthioethyl sulfoxide was dissolved in 3.5 ml. of ethanol, and with the addition of 1.5 ml. of 15N dilute sulfuric acid, the solution was allowed to stand overnight at room temperature. The resulting p-bromophenylacetaldehyde was converted by a customary method to 2,4-dinitrophenylhydrazone, and quantitatively analyzed. Amount yielded 126 mg. Yield 79.1%. The product was identified by infrared spectrography.

EXAMPLE 6

270 mg of methyl 1-methylthio-2-phenylethyl sulfoxide was dissolved in 4 ml. of ethanol, and with the addition of 0.390 ml. of ethyl orthoformate and 3 drops of concentrated sulfuric acid, the solution was heated at 54°C. for 1.5 hours. 500 mg of sodium hydrogencarbonate was added, and the mixture was stirred for 30 minutes at room temperature, followed by concentration at reduced pressure. 10 ml. of methylene chloride was added to the residue, and the mixture was filtered. The filtrate was concentrated at reduced pressure to give 225 mg of light yellow liquid. By simple distillation (oil bath temperature 100°C./14 mmHg), 198 mg of a colorless liquid was obtained. This liquid was identified as a diethyl acetal of phenylacetaldehyde by the comparison of its infrared spectrum with that of the standard specimen. Yield 88.4%.

EXAMPLE 7

72 mg of methyl 1-methylthio-2-phenylethyl sulfoxide was dissolved in 2.5 ml. of ethanol, and with the addition of 0.5 ml. of 15N dilute sulfuric acid, the solution was allowed to stand at room temperature for 12 hours. The resulting phenylacetaldehyde was converted in a customary manner to 2,4-dinitrophenylhydrazone, and quantitatively analyzed. Amount yielded 73 mg. Yield 68.9%. The identification of the product was performed using infrared spectroscopy.

EXAMPLE 8

1.30 g of methyl 2-(3,4-isopropylidenedioxyphenyl)-1-methylthioethyl sulfoxide was dissolved in 20 ml. of tetrahydrofuran, and with the addition of 5 drops of concentrated sulfuric acid, the solution was heated at 50°C. for 9 hours. Since the unreacted reactant remained in a small amount, 5 drops of concentrated sulfuric acid was further added, and the mixture was stirred for 12 hours at room temperature. 1 ml. of water and an excess of sodium bicarbonate were added, and the mixture was stirred for 30 minutes, followed by filtration, and concentrated at reduced pressure. The product was subjected to column chromatography (silica gel, benzene and methylene chloride) to give 297 mg of (3,4-isopropylidenedioxyphenyl)acetaldehyde in a yield of 34.0%.

The product was converted to an adduct of it with sodium hydrogensulfite, and the adduct was converted into the aldehyde, followed by purification by distillation under reduced pressure. This product was used for analysis.

b.p. 105°C/3 mmHg colorless liquid
IR (neat): 1728 cm$^{-1}$
NMR (CCl$_4$): δ1.65 singlet (6H); 3.45 doublet (2H, J=3.7 Hz); 6.55 m (3H); 9.59 triplet (1H, J=3.7 Hz).

Elemental analysis for $C_{11}H_{12}O_3$: Calculated: C, 68.73; H, 6.29%. Found: C, 69.01; H, 6.27%.

EXAMPLE 9

1.014 g of methyl 2-(3,4-isopropylidenedioxyphenyl)-1-methylthioethyl sulfoxide was dissolved in 20 ml. of methanol, and with the addition of 2 ml. of 4N dilute sulfuric acid, the solution was heated at 40°C. for 10.5 hours. The reaction mixture was neutralized with sodium bicarbonate, dried with anhydrous sodium sulfate, and concentrated at reduced pressure. The product was subjected to column chromatography (silica gel, benzene) to give 213 mg of (3,4-isopropylidenedioxyphenyl)acetaldehyde and 153 mg of a dimethyl acetal of (3,4-isopropylidenedioxyphenyl)acetaldehyde. The yield of the (3,4-isopropylidenedioxyphenyl)acetaldehyde was 31.3%, and the yield of the dimethyl acetal was 18.1%. The nuclear magnetic resonance of the dimethyl acetal was as follows:

NMR (CCl$_4$): δ 1.61 singlet (6H); 2.67 doublet (2H, J=7.2 Hz); 3.24 singlet (6H); 4.34 triplet (1H, J=7.2 Hz); 6.49 singlet (3H).

EXAMPLE 10

740 mg of methyl 2-(3,4-isopropylidenedioxyphenyl)-1-methylthioethyl sulfoxide was dissolved in 10 ml. of methylene chloride, and with the addition of 10 drops of concentrated hydrochloric acid, the solution was stirred at room temperature for one hour and 40 minutes. The reaction mixture was neutralized with sodium bicarbonate, dried with anhydrous sodium sulfate, and concentrated at reduced pressure. The product was subjected to column chromatography (silica gel, benzene) to give 187 mg of (3,4-isopropylidenedioxyphenyl)acetaldehyde in a yield of 37.7%.

EXAMPLE 11

868 mg of methyl 2-(3,4-isopropylidenedioxyphenyl)-1-methylthioethyl sulfoxide was dissolved in 10 ml. of methanol, and with the addition of 5 ml. of 1N aqueous solution of sulfuric acid, the solution was heated at 45° – 50°C. for 4 hours. 20 ml of water was added, and the reaction mixture was neutralized with sodium bicarbonate, and extracted three times with 150 ml. of ether. The ether layer was dried with anhydrous sodium sulfate, and concentrated at reduced pressure. The product was subjected to column chromatography (silica gel, benzene and methylene chloride) to give 180 mg of (3,4-isopropylidenedioxyphenyl)acetaldehyde in a yield of 49.0%.

EXAMPLE 12

1.166 g of phenyl 2-(3,4-isopropylidenedioxyphenyl)-1-phenylthioethyl sulfoxide was dissolved in 10 ml. of tetrahydrofuran, and with the addition of 5 drops of concentrated hydrochloric acid, the solution was allowed to stand for 15 hours at room temperature. 50 ml. of ether was added for extraction purposes, and the extracted layer was washed with water, and then with an aqueous solution of sodium bicarbonate. The extract was dried with anhydrous sodium sulfate, concentrated at reduced pressure, and then subjected to column chromatography to give 240 mg (yield 44.4%) of (3,4-isopropylidenedioxyphenyl)-acetaldehyde.

EXAMPLE 13

234 mg of methyl 2-(3,4-isopropylidenedioxyphenyl)-1-methylthioethyl sulfoxide was dissolved in 15 ml. of benzene, and the solution was heated under reflux for 3.5 hours. After concentrating the reaction mixture at reduced pressure, the product was subjected to column chromatography (silica gel, benzene) to give 39 mg of (3,4-isopropylidenedioxyphenyl)acetaldehyde.

EXAMPLE 14

987 mg of methyl 2-(3,4-isopropylidenedioxyphenyl)-1-methylthioethyl sulfoxide was dissolved in 8 ml. of ethanol, and with the addition of 1.3 ml. of ethyl orthoformate and 6 drops of concentrated sulfuric acid, the solution was stirred at room temperature for 40 hours. 10 ml. of water was added, over the reaction mixture was extracted with methylene chloride. The organic layer was dried with anhydrous sodium sulfate, and concentrated at reduced pressure. 5 ml. of tetrahydrofuran and 20 ml. of 0.25N dilute sulfuric acid were added to the residue, and the mixture was stirred for 19.5 hours at room temperature, followed by extraction with methylene chloride. The organic layer was dried with anhydrous sodium sulfate, concentrated at reduced pressure, and then subjected to column chromatography (silicon gel, benzene) to give 432 mg of (3,4-isopropylidenedioxyphenyl)acetaldehyde in a yield of 65%.

EXAMPLE 15

2.05 g of phenyl 2-(3,4-isopropylidenedioxyphenyl)-1-phenylthioethyl sulfoxide was dissolved in 20 ml. of ethanol, and with the addition of 10 drops of concentrated sulfuric acid and 1.8 ml. of ethyl orthoformate, the solution was stirred at room temperature for 50 hours. 15 ml. of water was added, and the reaction mixture was extracted with methylene chloride. The organic layer was dried with anhydrous sodium sulfate, and concentrated at reduced pressure. 10 m. of tetrahydrofuran and 30 ml. of 0.25 N sulfuric acid were added to the residue, and the mixture was stirred for 24 hours at room temperature, followed by extraction with methylene chloride. The organic layer was dried with Glauber's salt, and concentrated at reduced pressure.

The resulting residue was subjected to column chromatography (silica gel, benzene and n-hexane) to give 580 mg of (3,4-isopropylidenedioxyphenyl)acetaldehyde in a yield of 60%.

EXAMPLE 16

2.08 g of methyl 2-(3,4-methylenedioxyphenyl)-1-methylthioethyl sulfoxide was dissolved in 20 ml. of 1,2-dimethoxyethane, and with the addition of 1.71 g of cupric chloride dihydrate, the solution was refluxed for 15 minutes. The solvent was removed by evaporation at reduced pressure, and 50 ml. of methylene chloride was added. The insoluble water was removed by filtration. The filtrate was concentrated at reduced pressure, and subjected to column chromatography (silica gel, benzene) to give 722 mg of (3,4-methylenedioxyphenyl)acetaldehyde in a yield of 45%.

The following Examples 17 to 26 illustrate the production of sulfoxides of formula (II) by reacting halo-compounds of formula (III) with compounds of formula (IV). The sulfoxides of formula (II) obtained by these Examples can be converted to aldehydes of formula (I) by acid hydrolysis in the same way as described in Examples 1 to 16.

EXAMPLE 17

1.175 g of methyl methylthiomethyl sulfoxide was dissolved in 5 ml. of tetrahydrofuran, and under cooling with ice, 0.965 g (one equivalent) of sodium hydride was added. The mixture was then stirred for 1 hour. 1.93 g of p-methoxybenzyl bromide (1 equivalent) was added, and the mixture was stirred for 22 hours at room temperature, followed by addition of 40 ml. of methylene chloride and 2 ml. of water. The reaction mixture was dried with sodium sulfate anhydride, and concentrated at reduced pressure. The residue was subjected to column chromatography (silica gel, methylene chloride) to give 1.163 g of methyl 2-(p-methoxyphenyl)-1-methylthioethyl sulfoxide in a conversion yield of 79.1%.

It was confirmed by IR and NMR that this product is a 1:1 mixture of two diastereomers.

IR (film): $v$ SO 1037 cm$^{-1}$
NMR (CDCl$_3$): $\delta$ 7.05 A$_2$B$_2$ quartet (4H); 3.81 singlet (3H); 3.8–2.2 m (3H); 2.74 singlet (3/2H); 2.61 singlet (3/2H); 2.17 singlet (3/2H); 2.14 singlet (3/2H).

EXAMPLE 18

590 mg of methyl methylthiomethyl sulfoxide was dissolved in 5 ml. of tetrahydrofuran, and under cooling with ice, 171 mg (1.5 equivalents) of sodium hydride was added. The mixture was stirred for 1 hour. 813 mg of benzyl chloride was added, and the mixture was stirred at room temperature for 15 hours. 50 ml of methylene chloride and 1 ml. of water were added, and the reaction mixture was dried with anhydrous sodium sulfate, and the organic layer was concentrated at reduced pressure. The residue was subjected to column chromatography (silica gel, methylene chloride and ethyl acetate) to give 659 mg of methyl 1-methylthio-2-phenylethyl sulfoxide in a conversion yield of 92.2%.

NMR (CCl$_4$): $\delta$ 7.22 singlet (5H); 3.8–2.2 m (3H); 2.63 singlet (3/2H); 2.48 singlet (3/2H); 2.14 singlet (3/2H); 2.09 singlet (3/2H).

EXAMPLE 19

1.182 g of methyl methylthiomethyl sulfoxide was dissolved in 5 ml. of tetrahydrofuran, and under cooling with ice 229 mg (1.0 equivalent) of sodium hydride was added. The mixture was stirred for one hour. 1.91 g of p-bromobenzyl bromide (0.8 equivalent) was added, and the mixture was further stirred for 13 hours at room temperature. 50 ml. of methylene chloride was added, and the resulting precipitate was filtered. The filtrate was concentrated at reduced pressure, and subjected to column chromatography (silica gel, methylene chloride) to give 698 mg of methyl 2-(p-bromophenyl)-1-methylthioethyl sulfoxide in a yield of 36.5%.

NMR (CDCl$_3$): $\delta$ 7.32 A$_2$B$_2$ quartet (4H), 3.8–2.2 m (3H); 2.77 singlet (3H); 2.13 singlet (3H).

EXAMPLE 20

1.284 g of methyl methylthiomethyl sulfoxide was dissolved in 10 ml. of tetrahydrofuran, and under cooling with ice, 324 mg of sodium hydride was added. The mixture was stirred for one hour. Then, 2.545 g of 3,4-isopropylidenedioxybenzyl bromide was added, and the mixture was stirred for 19.5 hours at room temperature. 50 ml. of methylene chloride was added, and the resulting precipitate was separated by filtration. The filtrate was concentrated at reduced pressure, and subjected to column chromatography (silica gel, methylene chloride) to give 1.152 g of methyl 2-(3,4-isopropylidenedioxyphenyl)-1-methylthioethyl sulfoxide.

EXAMPLE 21

2.00 g of methyl methylthiomethyl sulfoxide was dissolved in 10 ml. of tetrahydrofuran, and under cooling with ice, 388 mg of sodium hydride was added, and the mixture was stirred for 1 hour, followed by heating at 50°C. for 20 minutes. The temperature was lowered to room temperature, and 3.17 g of 3,4-isopropylidenedioxybenzyl bromide was added, and the mixture was stirred for 19 hours. 50 ml. of methylene was added, and the resulting precipitate was filtered. The filtrate was concentrated at reduced pressure, and the then subjected to column chromatography (silica gel, methylene chloride) to give 1.485 g of methyl 2-(3,4-isopropylidenedioxyphenyl)-1-methylthioethyl sulfoxide.

EXAMPLE 22

3.02 g of methyl methylthiomethyl sulfoxide was dissolved in 10 ml. of tetrahydrofuran, and under cooling with ice, 760 mg of sodium hydride was added. The mixture was stirred for 15 minutes, followed by further stirring for 15 minutes at room temperature. 7.30 g of 3,4-isopropylidenedioxybenzyl) bromide was added, and the mixture was stirred for 17.5 hours at 30°C. 50 ml. of methylene chloride was added, and the resulting precipitate was filtered. The filtrate was concentrated at reduced pressure, and subjected to column chromatography to give 4.41 g of methyl 2-(3,4-isopropylidenedioxyphenyl)-1-methylthioethyl sulfoxide (conversion yield 73.5%). This sulfoxide is a mixture of two stereoisomers in a proportion of about 1:1 as determined by NMR. By crystallization from carbon tetrachloride, one of the stereoisomers could be isolated.

Colorless crystals m.p. 107.5 - 108.5°C.

NMR (CDCl$_3$): δ 1.68 singlet (6H); 2.17 singlet (3H); 2.75 singlet (3H); 3.2–3.8 m (3H; 6.69 singlet (3H).

IR (KBr): 1032 cm$^{-1}$

Elemental analysis for C$_{13}$H$_{18}$O$_3$S$_2$: Calculated: C, 54.51; H, 6.34; S, 22.39 Found: C, 54.28; H, 6.20; S, 22.28.

EXAMPLE 23

2.13 g of methyl methylthiomethyl sulfoxide was dissolved in 7.5 ml. of tetrahydrofuran, and under cooling with ice, 413 mg of sodium hydride was added. The mixture was stirred for 30 minutes under cooling with ice, and for another 30 minutes at room temperature, followed by addition of 3.23 g of 3,4-isopropylidenedioxybenzyl bromide. The mixture was stirred for 14 hours at room temperature, and for 2 hours at 30°C. 100 ml. of methylene chloride and 2 ml. of water were added, and the resulting mixture was dried with anhydrous sodium sulfate. After filtration, the filtrate was concentrated at reduced pressure, and the residue was subjected to column chromatography (silica gel, methylene chloride) to give 2.42 g of methyl 2-(3,4-isopropylidenedioxyphenyl)-1-methylthioethyl sulfoxide.

EXAMPLE 24

1.30 g of methyl methylthiomethyl sulfoxide was dissolved in 5 ml. of tetrahydrofuran, and a tetrahydrofuran solution containing 1.057 g of phenyl lithium was added. The mixture was stirred for 30 minutes under cooling with ice, and for 30 minutes at room temperature, followed by adding 1.92 g of 3,4-isopropylidenedioxyphenyl chloride. The mixture was stirred for one hour at room temperature, 13 hours at 35°C., and for additional 8.5 hours at 48°C. 50 ml. of methylene chloride was added, and the resulting precipitate was filtered. The filtrate was concentrated at reduced pressure, and then subjected to column chromatography (silica gel, methylene chloride) to give 619 mg of methyl 2-(3,4-isopropylidenedioxyphenyl)-1-methylthioethyl sulfoxide.

EXAMPLE 25

Example 25 was repeated except that butyl lithium was used instead of the phenyl lithium as a 20% n-hexane solution in an amount of 5.8 ml. There was obtained 575 mg of methyl 2-(3,4-isopropylidenedioxyphenyl)-1-methylthioethyl sulfoxide.

EXAMPLE 26

2.48 g of phenyl phenylthiomethyl sulfoxide was dissolved in 10 ml. of tetrahydrofuran, and under cooling with ice 240 mg of sodium hydride was added. The mixture was stirred for one hour. 2.43 g of 3,4-isopropylidenedioxybenzyl bromide was added, and the mixture was stirred for 18 hours at room temperature. 50 ml. of methylene chloride was added, and the resulting precipitate was filtered. The filtrate was concentrated at reduced pressure, and subjected to column chromatography (silica gel, methylene chloride) to give 3.44 g of phenyl 2-(3,4-isopropylidenedioxyphenyl)-1-phenylthioethyl sulfoxide.

The following Example illustrate the production of the aldehyde of formula (I) by reacting the halocompound of formula (III) with the compound of formula (IV) to form the sulfoxide of formula (II), and subjecting the resulting reaction mixture to acid hydrolysis without isolating the sulfoxide therefrom.

EXAMPLE 27

1.80 g of isopropyl isopropylthiomethyl sulfoxide was dissolved in 15 ml. of tetrahydrofuran, and under cooling with ice, 240 mg of sodium hydride was added, and the solution was stirred for one hour. 2.31 g of 3,4-dimethoxybenzyl bromide was added, and the mixture was stirred for 20 hours at room temperature, and for 3 hours at 35°C. 100 ml. of methylene chloride was added. After separating the insoluble water by filtration, the filtrate was concentrated at reduced pressure. The residue was dissolved in 20 ml. of tetrahydrofuran, and with the addition of 10 drops of concentrated sulfuric acid, the solution was stirred for 10 hours at 50°C. 500 mg of sodium bicarbonate was added, and the mixture was stirred for 30 minutes at room temperature. Then, the insoluble matter was separated by filtration. The filtrate was concentrated at reduced pressure, and the residue was subjected to column chromatography to give 631 mg of (3,4-dimethoxyphenyl)acetaldehyde in a yield of 35%.

The following example shows the preparation of Dopa by the Strecker reaction of (3,4-isopropylidenedioxyphenyl)acetaldehyde, which is one of the aldehyde products in accordance with the present invention.

8 ml. of methanol and 4 ml. of water were added to 477 mg of (3,4-isopropylidenedioxyphenyl)acetaldehyde, and 240 mg of sodium cyanide was further added. The mixture was acidified with 1N dilute sulfuric acid, and then rendered weakly alkaline with 4N-sodiumhydroxide aqueous solution. The mixture was then stirred for one hour at 0°C., and then for 10 hours at room temperature. The reaction mixture was extracted with methylene chloride. The organic layer was dried with anhydrous sodium sulfate, and concentrated at reduced pressure to give 538 mg of a light yellow oily matter. It was confirmed from IR and NMR that this product is 2-hydroxy-3-(3',4'-isopropylidenedioxyphenyl)propionitrile.

535 mg of the 2-hydroxy-3-(3',4'-isopropylidenedioxyphenyl)propionitrile was dissolved in 3 ml. of methanol, and the solution was saturated with ammonia gas. The solution was allowed to stand for 4 hours at room temperature. 5 ml. of water was added, and the resulting mixture was extracted with ether. The ether layer was washed with water, dried with anhydrous sodium sulfate, and concentrated at reduced pressure to give 487 mg of a light yellow oily matter. For analytical purposes, a part of the oily matter was purified. It was confirmed from IR and NMR that this product is 2-amino-3-(3',4'-isopropylidenedioxyphenyl)propionitrile.

IR (film): 3370, 3300, 1607, 1500, 1449, 1380, 1258, 1238, 1220, 1160, 982, 838 cm$^{-1}$ NMR (CDCl$_3$): δ 1.67 singlet (6H); 1.5–2.0 broad peak (2H); 2.92 doublet (2H, J=6.7 Hz); 3.89 triplet (1H, J=6.7 Hz); 6.67 singlet (3H). 225 mg of the above 2-amino-3-(3',4'-isopropylidenedioxyphenyl)propionitrile was dissolved in 5 ml. of 6N-hydrochloric acid, and the solution was refluxed for 2 hours. The reaction mixture was concentrated at reduced pressure to about one milliliter. It was saturated with ammonia gas, concentrated at reduced pressure, dried, and washed with hot alcohol to give 178 mg of 3-(3',4 -dioxyphenyl)DL-alanine having a melting point of 233° – 245°C (decomp.). The yield was 88%. By recrystallizing the product from water, a pure product having a

What is claimed is:

1. A method of preparing a dimethyl acetal or diethyl acetal of an aldehyde of the formula

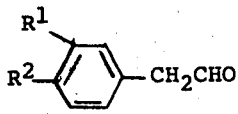

wherein $R^1$ is a member selected from the group consisting of hydrogen and alkoxy having 1 to 4 carbons, $R^2$ is a member selected from the group consisting of hydrogen, halogen and alkoxy having 1 to 4 carbons, and $R^1$ and $R^2$ together represent alkylidenedioxy having 1 to 4 carbons; which comprises the steps of subjecting to an acidic hydrolysis and acetalization a sulfoxide of the formula

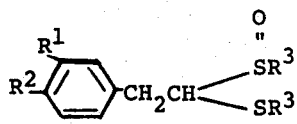

wherein $R^1$ and $R^2$ have the above meanings, and the two $R^3$ groups are the same and each selected from the group consisting of alkyl having 1 to 4 carbons and phenyl, said acidic hydrolysis and acetalization being carried out in the presence of mineral or organic protic acids having a pK smaller than about 1 or Lewis acids and in the copresence of an acetalization agent selected from the group consisting of methyl orthoformate and ethyl orthoformate to produce the objective acetal compound.

2. A method according to claim 1, wherein the resulting acetal is further treated with an acid to convert it to the corresponding aldehyde of the formula

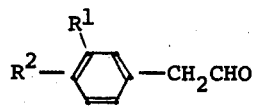

wherein $R^1$ and $R^2$ have the same meanings defined in claim 1.

* * * * *